United States Patent [19]

Dastoor et al.

[11] 4,363,188
[45] Dec. 14, 1982

[54] ENHANCEMENT OF IN VITRO GUAYULE PROPAGATION

[76] Inventors: Alan M. Lovelace, Administrator of the National Aeronautics and Space Administration, with respect to an invention of Minoo N. Dastoor, San Marino, Calif.; Wayne W. Schubert, Los Angeles, Calif.; Gene R. Petersen, Pasadena, Calif.

[21] Appl. No.: 280,153

[22] Filed: Jun. 30, 1981

[51] Int. Cl.³ .......................... A01N 9/12; A01G 1/00
[52] U.S. Cl. ........................................... 47/58; 71/98
[58] Field of Search ................ 47/58; 71/98, 86, 106, 71/111, 121

[56] References Cited
U.S. PATENT DOCUMENTS 4,159,903 7/1979 Bauman.

OTHER PUBLICATIONS

Bonner, J. A. and B. Arreguin, *Arch. Biochem.*, 26, 178–186 (1950).
Yokoyama, H. et al, *Science*, 197, 1076–1078, (1977).
Gamborg, O. L. et al, *In Vitro*, 12, 473–478, (1976).

*Primary Examiner*—Robert E. Bagwill
*Attorney, Agent, or Firm*—Paul F. McCaul; John R. Manning; Thomas H. Jones

[57] ABSTRACT

Stimulation the in vitro propagation of Guayule from a nutrient medium containing Guayule tissue by adding a substituted trialkyl amine bioinducing agent to the nutrient medium. Selective or differentiated propagation of shoots or callus is obtained by varing the amounts of substituted trialkyl amine present in the nutrient medium. The luxuriant growth provided may be processed for its poly isoprene content or may be transferred to a rooting medium for production of whole plants as identical clones of the original tissue. Provides method for producing large numbers of Guayule plants having identical desirable properties such as high polyisoprene levels.

9 Claims, 1 Drawing Figure

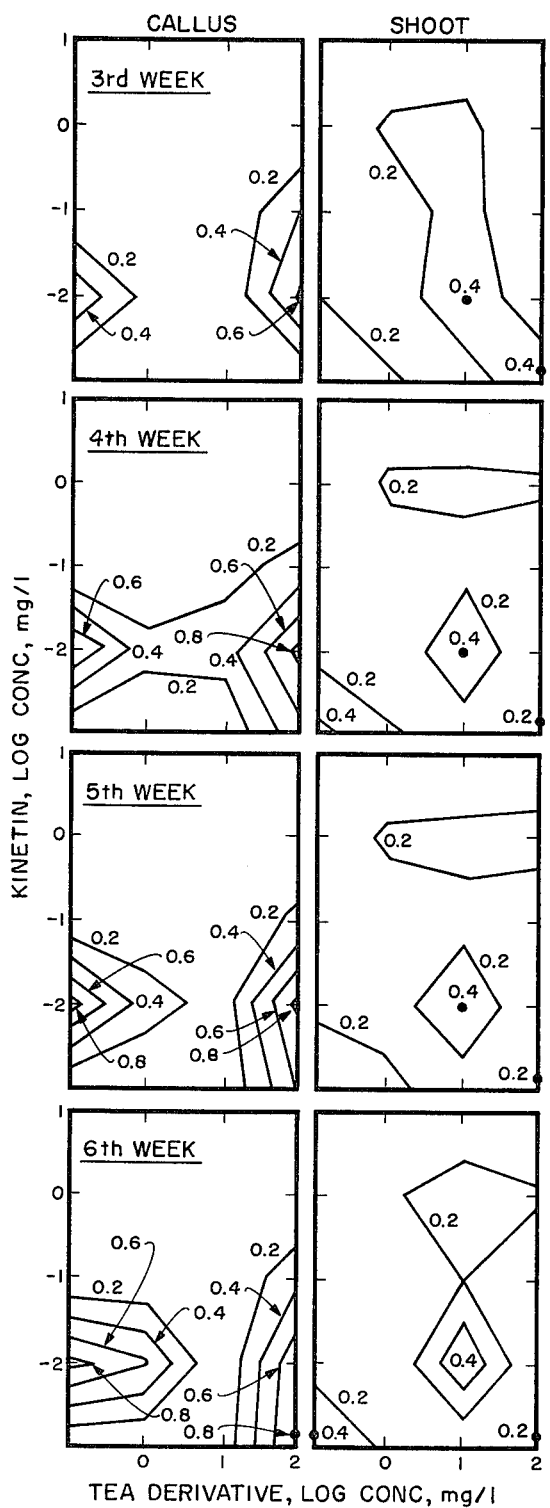

ENHANCEMENT OF IN VITRO GUAYULE PROPAGATION

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to plant growth regulators, and more particularly, to the enhancement of production of polyisoprene rubber by stimulation of in vitro propagation of Guayule callus and shoots from a nutrient containing Guayule tissue.

2. Description of the Prior Art

Guayule is a desert shrub native to the southwestern United States and northern Mexico that produces polymeric isoprene essentially identical to that made by Hevea rubber trees in Southeast Asia. As recently as 1910 it was the source of half of the natural rubber used in the U.S. Since 1946, however, its use as a source of rubber has been all but abandoned in favor of cheaper Hevea rubber and synthetic rubbers. However, demand for natural rubber is expected to produce shortages of that material and rubber prices are expected to double by 1985. Natural rubber having lower heat hysteresis is required for many kinds of tires and amounts to about 35% of U.S. rubber use.

It is technically possible to satisfy projected demand with synthetics, but the rise in world petroleum prices has prompted the rubber industry to look for alternative sources of natural rubber. The principal, if not the only such, source is Guayule. It is conceivable that Guayule eventually could replace Hevea trees because of the susceptibility of the Hevea tree to a number of devastating diseases.

To minimize dependence on dwindling supplies of fossil fuel, attention is being directed to the production of hydrocarbons in plants such as Hevea and Guayule.

Guayule plants thrive on the dry, sandy soil of southwestern U.S. and Mexico. During World War II, extensive plantings of Guayule were carried out in California, near Indio and Salinas. Guayule normally yields one half ton of rubber per acre in cultivation when, after two years, the entire plant is harvested and processed.

Because natural Guayule has a two year harvest cycle and can only be grown in a few selected areas of warm climate regions in Arizona, California and Mexico there have been numerous attempts to speed up the growth rate and yield of valuable polyisoprene rubber contained in the plant. For example, U.S. Pat. No. 4,159,903 issued to Bauman on July 3, 1979, discloses a growth enhancement procedure wherein a 400% increase in polyisoprene rubber yields from Guayule plants is obtained by administering substituted trialkylamines to the plants. Although this method provides increased polyisoprene production, it is still limited to naturally grown Guayule grown in warm climate regions. It is therefore desirable to provide a method for propagating Guayule in vitro in an industrial setting not limited to specific climate conditions and geographical location.

Guayule has been established in vitro in tissue cultures by J. A. Bonner and B. Arreguin, Arch. Biochem., 26, 1978-186 (1950). Propagation of whole Guayule plants including roots has not been achieved. The propagation of Guayule has been limited to the establishment and maintenance of Guayule callus and shoots. Since polyisoprene is distributed throughout the entire Guayule plant including the callus and shoots, harvesting and processing according to known pyrolysis or extraction techniques of the in vitro generated callus and shoots provides a potentially useful source of polyisoprene. A further advantage of promoting in vitro propagation of Guayule callus and shoots is the potential cloning of a single species of Guayule known to have high rubber levels to produce many clones having the identical desired high rubber levels. These clones may then be planted, grown and harvested commercially. Accordingly, any method which stimulates, enhances or otherwise promotes in vitro propagation of Guayule callus and shoots is desirable.

SUMMARY OF THE INVENTION

In accordance with the present invention, a method is provided for promoting in vitro propagation of Guayule which results in the luxuriant growth of callus and shoots which may be harvested and processed to provide polyisoprene or transferred to rooting media and grown conventionally.

The present invention is based on the discovery that a suitable nutrient medium containing Guayule tissue when treated with substituted trialkyl amines produces a luxuriant growth of Guayule callus and shoots. As a particular feature of the present invention, it has been found that by varying the concentration of the substituted trialkyl amine in the tissue culture it is possible to produce shoots or callus exclusively. At concentrations of substituted trialkyl amine near 10 mg. per liter of nutrient or basal media, propagation of shoots substantially exclusive of callus occurs. At substituted trialkyl amine concentrations below and above the 10 mg. per liter level the propagation of callus substantially exclusive of shoots occurs. As is apparent, by selecting appropriate levels of substituted trialkyl amines, differential and selective propagation of Guayule shoots or callus is possible.

The method of the present application is particularly useful, since although it does not yet provide for in vitro propagation of whole Guayule plants, it does provide a method for enhancing and stimulating differentiated propagation and growth of Guayule for the production of polyisoprene in a controlled environment without the environmental and geographical problems inherent in natural growth of the Guayule plant. Furthermore, a significant advantage of the present invention is the use of given nutrients and trialkyl amine to produce shoots from tissue which can then be transferred to rooting media with the rooted plants thus formed being transplanted and grown in a greenhouse or the like. In this way, many entire plants may be cloned from the tissue of a plant strain having known high rubber level thereby enhancing the overall polyisoprene production possible for a given crop of plants. The above discussed and many other features and attendant advantages of the present invention will become apparent as the invention becomes better understood by reference to the following detailed description.

BRIEF DESCRIPTION OF THE DRAWING

The drawing is a three dimensional graphic display of the observations made in the matrix shown in Table 5.

DESCRIPTION OF THE INVENTION

The present invention involves enhanced Guayule propagation in suitable nutrient or basal media by treatment with substituted trialkyl amines.

Any number of isotonic, buffered, nutrient media containing mineral salts as macronutrients and micronutrients, hormones, vitamins and supplements may be utilized in accordance with the present invention so long as they are capable of supporting propagation of Guayule from appropriate tissue. However, it is preferred that those media developed by Murashige and Skoog and Schenk and Hildebrandt as described by O. L. Gamborg, et al. (In Vitro, 12, 473–478 (1976) be utilized. Among the preferred nutrient media, two particular nutrient medias are preferred. These two media are designated MS(15) and SH(26). The ingredients and their concentrations and pH for each media are set forth in TABLES 1, 2 and 3.

TABLE 1
MINERAL SALT MEDIA FOR GUAYULE TISSUE CULTURES

| Salts | MS(15) 1 | | SH(26) 4 | |
|---|---|---|---|---|
| Macronutrients | $\frac{mg}{L}$ | mM | $\frac{mg}{L}$ | mM |
| $NH_4NO_3$ | 1650 | 20.6 | | |
| $KNO_3$ | 1900 | 18.8 | 2500 | 25 |
| $CaCl_2.2H_7O$ | 440 | 3.0 | 200 | 1.4 |
| $MgSO_4.7H_7O$ | 370 | 1.5 | 400 | 1.6 |
| $KH_2PO_4$ | 170 | 1.25 | | |
| $NH_4H_2PO_4$ | | | 300 | 2.6 |
| Micronutrients | $\frac{mg}{L}$ | $\mu M$ | $\frac{mg}{L}$ | $\mu M$ |
| KI | 0.83 | 5.0 | 1.0 | 6.0 |
| $H_3BO_3$ | 6.2 | 100 | 5.0 | 80 |
| $MnSO_4.4H_2O$ | 22.3 | 100 | | |
| $MnSO_4.H_2O$ | | | 10 | 60 |
| $ZnSO_4.7H_2O$ | 8.6 | 30 | 1.0 | 3.5 |
| $Na_2MoO_4.2H_2O$ | 0.25 | 1.0 | 0.1 | 0.4 |
| $CuSO_4.5H_2O$ | 0.025 | 0.1 | 0.2 | 0.8 |
| $CoCl_2.6H_2O$ | 0.025 | 0.1 | 0.1 | 0.4 |
| $Na_2.EDTA$ | 37.3 | 100 | 20 | 55 |
| $FeSO_4.7H_2O$ | 27.8 | 100 | 15 | 55 |
| Sucrose (g) | 30 | | 30 | |
| pH | 5.7 | | 5.8 | |

TABLE 2
AMOUNTS AND KINDS OF VITAMINS, HORMONES AND SUPPLEMENTS USED WITH THE MINERAL SALT MEDIA

| Compound | MS(15) $\frac{mg}{L}$ | SH(26) $\frac{mg}{L}$ |
|---|---|---|
| Inositol | 100 | 1000 |
| Nicotinic Acid | 0.5 | 5.0 |
| Pyridoxine.HCl | 0.5 | 0.5 |
| Thiamine.HCl | 0.1 | 5.0 |
| Glycine | 2.0 | |
| IAA[a] | 1–30 | |
| NAA[b] | | |
| Kinetin | 0.04–10 | |
| 2,4-D[c] | | 0.5 |
| p-CPA[d] | | 2.0 |

[a]Indoleacetic acid.
[b]Naphthaleneacetic acid.
[c]2,4-Dichlorophenoxyacetic acid.
[d]p-chlorophenoxyacetic acid.

TABLE 3
CONCENTRATIONS OF INORGANIC NUTRIENTS IN MEDIA FOR PLANT TISSUE CULTURE

| | MS | SH |
|---|---|---|
| Macro-Nutrients (mM) | | |
| K | 20 | 25 |
| $N(NO_3)$ | 40 | 25 |
| $N(NH_4)$ | 20 | 2.6 |
| Mg | 1.5 | 1.6 |
| P | 1.25 | 2.6 |
| Ca | 3.0 | 1.4 |
| S | 1.5 | 1.6 |
| Na | — | — |
| Cl | 6.0 | 2.0 |
| Micro-Nutrients ($\mu M$) | | |
| I | 5.0 | 6.0 |
| B | 100 | 80 |
| Mn | 100 | 60 |
| Zn | 30 | 3.5 |
| Mo | 1.0 | 0.4 |
| Cu | 0.1 | 0.8 |
| Co | 0.1 | 0.4 |
| Al | | |
| Ni | | |
| Fe | 100 | 55 |

As set forth in Table 2, the concentration of IAA and Kinetin in the nutrient media may be varied within certain limits and still support Guayule propagation. Table 4 sets forth the results of tissue culture work where IAA and Kinetin levels were varied.

TABLE 4
EFFECTS OF DIFFERENT MEDIA ON CALLUS AND ROOT FORMATION

| | A | B | C | D | E | F | G |
|---|---|---|---|---|---|---|---|
| CALLUS | 0.80 ±0.23 | 0.84 ±0.15 | 0.94 ±0.10 | 0.02 ±0.04 | 0.05 ±0.10 | 0.00 ±0.00 | 0.90 ±0.22 |
| SHOOT | 0.09 ±0.11 | 0.09 ±0.14 | 0.18 ±0.17 | 0.51 ±0.22 | 0.64 ±0.42 | 0.12 ±0.13 | 0.05 ±0.11 |
| ROOT | — | — | — | — | — | — | — |
| IAA | 4.0 mg/l | 4.0 mg/l | 1.0 mg/l | — | — | — | — |
| KINETIN | 2.56 mg/l | 2.56 mg/l | 0.04 mg/l | 0.1 mg/l | 0.1 mg/l | 0.1 mg/l | — |
| 2,4-D | — | — | — | — | — | — | 0.5 mg/l |
| pCPA | — | — | — | — | — | — | 2.0 mg/l |
| TEA DERIV. | — | — | — | — | 10 mg/l | 1 mg/l | — |
| BASAL MEDIUM | MS | MS | MS | MS | MS | MS | SH |
| pH | 5.7 | 4.9 | 5.7 | 5.7 | 5.7 | 5.7 | 5.7 |
| SUCROSE | 30 g | 15 g | 30 g | 30 g | 30 g | 30 g | 30 g |

Explants for the tissue culture work were obtained from juvenile Guayule plants that ranged 15–50 cm in height and were 3-9 months old. Shoot tissue was obtained from several sources including Guayule shoot tips, sections from young shoots and more mature stems. Callus formation in stem segments of both nodal and internodal regions usually showed cell division in the pith and cambium regions primarily above but occasionally below the agar line. Formation of callus occurred after 7-10 days. Adventitious shoots developed in stem tissue at internodal and nodal points and at the end of segments above the agar line.

Each value in Table 4 represents the mean average of at least three separate observations with each observation comprised of a group of 2-40 slants containing stem tissue. The standard deviation is included. The group of slants were randomly placed in a growth area illuminated on L/D 16:8. The temperature and humidity varied during this cycle between 29° C. and 31% humidity during light cycles to 25° C. and 35% humidity in the dark cycles as measured by a Foxboro temperature and relative humidity meter.

The slants were scored after a minimum of 14 days incubation and the fraction of tubes containing callus and/or shoots were recorded. Columns A, B, C, D show that selective formation of Guayule shoots and/or callus can be controlled by varying the IAA and Kinetin levels.

The tissue cultures of columns A, B, C and D included the MS(15) mineral salt or basal medium. Tissue culture tests as described above were also conducted to determine Guayule shoot and callus propagation in the SH(26) basal media. The results of these tests are listed in column G of Table 4. As can be seen from Table 4, both the MS and SH basal medias are suitable for Guayule callus and/or shoot propagation. Other similar media would also be expected to be suitable.

In accordance with the present invention, the selective propagation of Guayule callus or shoots in suitable media, such as MS(15) and SH(26), is enhanced by the addition of substituted trialkyl amines bioinduction agents to the tissue culture. The means by which the substituted trialkyl amines are introduced into the nutrient media is not important so long as the concentrations of the substituted trialkyl amine in the media are within described limits and are uniformly dispersed throughout the media.

The bioinduction agents of the invention are selected from amines of the formula:

$$R_1-\underset{\underset{R_3}{|}}{\overset{\overset{R_2}{|}}{N}}$$

where at least one of $R_1$, $R_2$ and $R_3$ is a hydrocarbon chain containing at least two carbon atoms. $R_1$, $R_2$ and $R_3$ may be hydrogen, alkyl of from 1 to 10 carbon atoms, aryl such as phenyl or $R_1$ may be a carboncarbon bond and $R_2$ and $R_3$ may be combined into a cyclic structure containing 1 to 10 carbon atoms and hetero atoms such as oxygen, nitrogen, sulfur such as pyridine, P-ethyl pyridine, 2,4,dichloropyridine or imidazole.

Preferred polyisoprene bioinducing agents of the invention are trialkyl amines of the formula:

$$R_4-\underset{\underset{R_5}{|}}{N}-R_6$$

where $R_4$ and $R_5$ are alkyl of 1 to 10 carbon atoms preferably ethyl and at least one of $R_4$, $R_5$ and $R_6$ are substituted with an electron withdrawing group such as halogen, preferably chloro, iodo or bromo, nitro, carbonyl, aldehyde, alkoxy, aryloxy and thio analogs thereof. At least one of $R_4$, $R_5$ and $R_6$ has the structure $-CH_2-(CH_2)qR_7$ where q is an integer from 1 to 6 and $R_7$ is hydrogen, an electron withdrawing group, aryl such as phenyl, substituted phenyl such as $R_9Ph-$ where $R_9$ is alkyl of 1 to 6 carbon atoms or an electron withdrawing group and Ph is phenyl, $(CH_2)p-O-R_8$ and $(CH_2)p-S-R_8$ where p is an integer from 1 to 6 and $R_8$ is hydrogen, alkyl of 1 to 4 carbon atoms, aryl such as phenyl or $-Ph-R_9$. $R_4$, $R_5$ or $R_6$ may be substituted with various groups which do not interfere with systemic transport into the plant nor with the bioinduction activity such as phosphoric, sulfuric groups or esters thereof. The compounds can be administered to the nutrient media as the free base, salt, hydroxide or acid addition salt of hydrochloric or phosphoric acid.

Representative compounds are presented in the following table:

| Compounds | |
|---|---|
| 1 | 2-(4-chlorophenylthio)triethylamine hydrochloride (CPTA) |
| 2-6 | $Et_2N(CH_2)_qPh$, where Ph is phenyl and q = 1(2), 2(3), 3(4), 4(5), 5(6) |
| 7-11 | $Et_2NCH_2CH_2OC_6H_4-R_6$ where $C_6H_4$ is phenylene and $R_6$ = H(7), p-Me(8), p-Et(9), p-iso-Pr(10) and p-tert-Bu(11) |
| 12-14 | $Et_2NCH_2CH_2O-C_6H_4OCOR_7$ where $C_6H_4$ is phenylene and $R_7$ is H(12), Me(13) or $C_6H_5(14)$ |
| 15 | Choline |
| 16 | N,N—diacetylethanolamine phosphate |
| 17 | 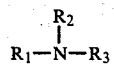 |
| 18 | $Et_2N-\underset{\underset{\underset{\underset{}{}}{}}{C=O}}{\overset{\overset{CH_3}{|}}{\underset{|}{C}}}-H$ |
| 19 | $Et_2-\overset{-O}{\underset{+}{N}}-CH_2CH_2-O-\bigcirc-Cl$ |
| 20 | $N(CH_2CH_2-S-\bigcirc-Cl)_3$ |
| 21 | $Et_2N-CH_2CH_2-O-\bigcirc-Cl$ |
| 22-24 | $Et_2NCH_2CH_2-O-X$ where X = 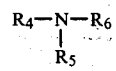 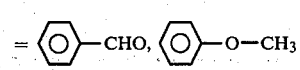 |
| 25 | $Et_2N.HCl$ |
| 26 | $Bu_3N.HCl$ |

-continued

| Compounds | |
|---|---|
| 27 | 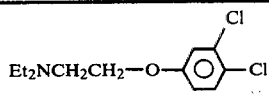 |

The bioinducers of the invention are generally applicable to increasing the production of polyisoprene having a molecular weight above 300,000 typically about 2,000,000 in plants such as Guayule (Parthenium argentatum Gray), Hevea (Hevea brasiliensis Muell), Euphorbia tirucalli and Russian dandelion (Taraxacum kox saghz Rodin).

A particularly preferred bioinductive agent regulator is 2-(3,4-dichlorophenoxy)-triethylamine (TEA). As shown in Table 4 at columns E and F, TEA was added to the nutrient medium of column D. The result was a luxuriant growth of Guayule shoots.

To quantify the effect of the TEA derivative on callus formation and organogenesis, a matrix experiment was devised to test the action and interaction of kinetin and TEA over a broad range of concentrations. Table 5 presents the results of this experiment.

The matrix represents twenty separate observations that were conducted simultaneously. Each of the twenty observations utilized a different kinetin and TEA derivative level with 10-15 separate slants containing tissue per observation. The basal medium was an MS medium (see Columns E and F in Table 4). The growth conditions were as described for the tests in Table 4.

Each point is the mean average of the fraction of slants containing callus or shoots found for two successive weeks of observation commencing 21 days after innoculation. Thus, the observations were conducted at 3, 4, and 5 weeks after innoculation. The C and S designations signify callus and shoot respectively.

were conducted simultaneously. Each of the twenty observations utilized a different kinetin and TEA derivative level with 10-15 separate slants containing tissue per observation. The basal medium was an MS medium (see columns E and F in Table 4) and growth conditions were as described in Table 4.

The mean average of fraction of slants containing callus or shoots found for three successive weeks of observation commencing 21 days after inoculation was measured. Thus, the observations were conducted at 3, 4, 5 and 6 weeks after inoculation.

Each week of observation of the matrix experiment was plotted on a contour plot. The contour lines connect the observations which have identical levels of callus or shoot formation. The numerical value ascribed to each contour line indicates the fraction of callus or shoots in the observation. The uppermost set of graphs represents the observation at 3 weeks after inoculation and each succeeding set of plots represents observations at one week (+/− 2 days) after this initial observation. Infected slants are removed from consideration as they occur and thus the low level of callus at the 4th week in the 10 mg/l TEA range disappears in succeeding weeks. The significant factor is that at the other derivative concentrations, new callus formation increases while at this specific level no new callus formation occurs.

As shown in FIG. 1 and Table 5, suppression of callus formation occurs at a 8-12 mg/l concentration of TEA derivative with a resultant increase of shoot formation. Lower and higher concentrations of TEA derivative promote callus formation. Therefore, when it is desired to enhance shoot propagation only, the concentration of TEA in the nutrient media should be maintained between about 8 mg/l and 12 mg/l and preferably at about 10 mg/l. When enhanced callus propagation only is desired, the TEA level is maintained either above or below 8-12 mg/l and preferably below 100 mg/l.

The present invention, therefore, not only provides a means for enhancing and increasing Guayule propaga-

TABLE 5

EFFECT OF KINETIN AND TEA DERIVATIVE ON CALLUS SHOOT FORMATION

| KINETIN (mg/l) | TEA (mg/l) | 0 C | 0 S | 1 C | 1 S | 10 C | 10 S | 100 C | 100 S | Mean Averages Callus-Top Shoots-Bottom |
|---|---|---|---|---|---|---|---|---|---|---|
| 0 | C | 0.00 ±0.00 | | 0.00 ±0.00 | | 0.00 ±0.00 | | 0.37 ±0.32 | | 0.09 ±0.22 |
| | S | | 0.41 ±0.05 | | 0.24 ±0.02 | | 0.07 ±0.00 | | 0.27 ±0.12 | 0.25 ±0.14 |
| 0.01 | C | 0.73 ±0.14 | | 0.24 ±0.10 | | 0.13 ±0.15 | | 0.76 ±0.12 | | 0.46 ±0.31 |
| | S | | 0.17 ±0.04 | | 0.05 ±0.04 | | 0.40 ±0.00 | | 0.00 ±0.00 | 0.16 ±0.16 |
| 0.1 | C | 0.00 ±0.00 | | 0.00 ±0.00 | | 0.04 ±0.08 | | 0.31 ±0.08 | | 0.09 ±0.14 |
| | S | | 0.17 ±0.00 | | 0.11 ±0.00 | | 0.18 ±0.08 | | 0.02 ±0.04 | 0.12 ±0.08 |
| 1.0 | C | 0.07 ±0.00 | | 0.00 ±0.00 | | 0.06 ±0.07 | | 0.00 ±0.00 | | 0.03 ±0.04 |
| | S | | 0.05 ±0.04 | | 0.23 ±0.00 | | 0.26 ±0.01 | | 0.18 ±0.16 | 0.18 ±0.11 |
| 10.0 | C | 0.00 ±0.00 | | 0.00 ±0.00 | | 0.00 ±0.00 | | 0.00 ±0.00 | | 0.00 ±0.00 |
| | S | | 0.00 ±0.01 | | 0.06 ±0.00 | | 0.03 ±0.05 | | 0.00 ±0.00 | 0.02 ±0.03 |
| Mean Averages Callus-left Shoots-right | | 0.16 ±0.30 | 0.16 ±0.15 | 0.05 ±0.10 | 0.14 ±0.09 | 0.05 ±0.09 | 0.19 ±0.14 | 0.29 ±0.32 | 0.10 ±0.14 | |

FIG. 1 is a three dimensional representation of the observations made in the matrix tabulated in Table 5. The matrix includes twenty separate observations that tion with increased polyisoprene production, but also allows selective or differentiated growth where callus or shoots may alternatively and selectively be propagated.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein.

What is claimed is:

1. A method of stimulating the in vitro propagation of polyisoprene containing plants from a nutrient medium containing polyisoprene containing plant tissue comprising the step of:
adding to said nutrient medium an amount effective to stimulate propagation of said polyisoprene containing plant of a bioinducing agent of the formula;

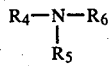

where $R_5$ and $R_6$ are selected from phenyl, $-CH_2(CH_2)_q R_7$ where q is an integer from 1 to 6, $R_7$ is hydrogen; phenyl; an electron withdrawing group; $R_9$ phenyl—where $R_9$ is alkyl of 1 to 6 carbon atoms or an electron withdrawing group; $-(CH_2)_p OR_8$ or $-(CH_2)_p S-R_8$ where p is an integer from 2 to 6, $R_8$ is hydrogen, alkyl of 1 to 4 carbon atoms, phenyl or phenyl $R_9$, and $R_4$ is hydrogen or $R_5$, and at least one of $R_4$, $R_5$ and $R_6$ has the structure: $-CH_2-(CH_2)_q-R_7$.

2. A method according to claim 1 wherein said polyisoprene containing plant is selected from the group consisting of Guayule, Hevea and Russian dandelion.

3. A method according to claim 2 wherein said polyisoprene containing plant is Guayule.

4. A method according to claim 3 wherein a selective amount of said bioinducing agent is added to said nutrient medium to stimulate differentiated growth of said Guayule.

5. A method according to claim 1 wherein said bioinducing agent is 2-(3,4-dichlorophenoxy)-triethylamine.

6. A method according to claim 4 for stimulating Guayule shoot propagation from said nutrient medium by adding sufficient 2-(3,4dichlorophenoxy)-triethylamine to said nutrient medium to provide a nutrient medium having between 8 and 12 mg/l of said 2-(3,4-dichlorophenoxy)-triethylamine.

7. A method according to claim 4 for stimulating Guayule callus propagation from said nutrient medium by adding 2-(3,4-dichlorophenoxy)-triethylamine to said nutrient medium in an amount sufficient to provide a nutrient medium having a 2-(3,4-dichlorophenoxy)-triethylamine concentration of below about 100 mg/l but not between 8 and 12 mg/l.

8. A method according to claim 1 wherein said nutrient medium contains mineral salts, vitamins, hormones and supplements.

9. A method according to claim 5 wherein said nutrient medium is selected from the group consisting of MS(15) and SH(26) media.

* * * * *